US010088400B2

(12) United States Patent
Peluso

(10) Patent No.: US 10,088,400 B2
(45) Date of Patent: Oct. 2, 2018

(54) GROUP FOR ALLOWING FREE ORIENTATION OF A SPHERE WITH RESPECT TO OUTSIDE FORCE FIELDS

(71) Applicant: TELESPAZIO S.p.A., Rome (IT)

(72) Inventor: Fabio Peluso, Naples (IT)

(73) Assignee: TELESPAZIO S.P.A., Rome (IT)

( * ) Notice: Subject to any disclaimer, the term of this patent is extended or adjusted under 35 U.S.C. 154(b) by 320 days.

(21) Appl. No.: 14/902,276

(22) PCT Filed: Jul. 1, 2013

(86) PCT No.: PCT/IT2013/000181
§ 371 (c)(1),
(2) Date: Dec. 30, 2015

(87) PCT Pub. No.: WO2015/001577
PCT Pub. Date: Jan. 8, 2015

(65) Prior Publication Data
US 2016/0202158 A1     Jul. 14, 2016

(51) Int. Cl.
*B64G 4/00* (2006.01)
*G01N 1/42* (2006.01)
*B64G 1/66* (2006.01)
*B01L 1/02* (2006.01)
*B64G 1/22* (2006.01)

(52) U.S. Cl.
CPC ............... *G01N 1/42* (2013.01); *B64G 1/66* (2013.01); *B64G 4/00* (2013.01); *B01L 1/02* (2013.01); *B64G 2001/228* (2013.01)

(58) Field of Classification Search
CPC ....................................................... B64G 4/00
See application file for complete search history.

(56) References Cited

PUBLICATIONS

G. Paul Neitzel et al., "Principles, Limits and Microgravity Applications for Self-Lubricated Liquids", SAO/NASA Astrophysics Data System (ADS), Jan. 1, 2001 (Jan. 1, 2001), Retrieved from the Internet: URL:http://articles.adsabs.harvard.edu/cgi-bin/nph-iarticle_query?2001ESASP.454..109N&defaultprint=YES&filetype=.pdf.
G. Paul Neitzel et al., "Noncoalescence and Nonwetting Behavior of Liquids" *Annual Review of Fluid Mechanics*, vol. 34(1):267-289, Jan. 1, 2002 (Jan. 1, 2002).

*Primary Examiner* — Robert R Raevis
(74) *Attorney, Agent, or Firm* — Seed IP Law Group LLP

(57) ABSTRACT

A group for allowing free orientation of a sphere with respect to outside force fields includes a support structure, a sphere, two locking elements acting from opposite sides on the sphere and useful to keep the sphere in a right position during a nonoperational phase of the group, at least four drop supports located around the sphere and able to form drops and to keep them at a desired temperature, and an isolation structure useful to isolate the above devices from the surroundings and to prevent dust deposition on the sphere surface and the four realized drops, and cooling device able to keep the sphere at a temperature lower than that of the drops.

12 Claims, 6 Drawing Sheets

GROUP FOR ALLOWING FREE ORIENTATION OF A SPHERE WITH RESPECT TO OUTSIDE FORCE FIELDS

BACKGROUND

Technical Field

The present invention relates to a group for allowing free orientation of a sphere with respect to outside force fields.

In particular, the group of the invention finds its main field of applicability as a device for experiments in microgravity.

Description of the Related Art

One can exploit the advantages of the reduced gravity field of the space environment to perform experiments sensitive to gravity or to reveal phenomena masked on the ground by the presence of gravity. Long duration experiments however, also in the reduced gravity field, may be slightly or highly affected by the effects of the residual gravity field present during the space navigation; moreover, during the navigation, the spaceships change their orientation with respect to the residual gravity field. This facts result in the presence of a disturbance, due to the residual gravity, that changes during the experiment, in modulus and orientation. Many times, this effect, that cannot be limited or eliminated, seriously affects the results of the experiments or complicates their elaboration.

Therefore the need was felt to make available a device whose technical features are able to overcome the above prior art technical problems.

The concept on which the present invention is based is the physical phenomenon of permanent inhibition of coalescence discovered years ago. In short, when a liquid drop is heated at a temperature higher than that of a solid surface to which the drop is approached, surface motions arise in the drop due to the variation with temperature of the liquid drop's surface tension. Studies performed have shown that such surface motions trap the air in between the drop surface and the solid one, giving rise to a soft, friction-less pillow.

BRIEF SUMMARY

Similar behavior is observed when two drops kept at different temperatures face each other: the two drops do not coalesce even if they are pushed one against the other.

The Applicant has exploited such a phenomenon in order to satisfy the above need.

The subject of the present invention is a device for experiments in a microgravity environment and a group for allowing free orientation of a sphere with respect to outside force fields. The group includes a support structure, a sphere, two locking elements acting from opposite sides on the sphere and useful to keep the sphere in a right position during a non-operational phase of the group, at least four drop supports located symmetrically around the sphere and able to form drops and to keep them at a desired temperature, an isolation sealed structure useful to isolate the above devices from the surrounding and to prevent dust deposition on the sphere surface and the four realized drops, and a cooling/filtering device useful to inject cool gas inside the isolation structure in order to keep the sphere at a temperature lower than that of the drops. The cooling/filtering device includes at least two inlet pipes facing into said isolation sealed structure by two respective inlet windows placed opposite one another with respect to the sphere in order to invest from opposite sides the sphere by a cool/filtered gas, and at least two outlet pipes each of them faces into the isolation sealed structure by a respective outlet window placed 90 degrees far from each of the inlet windows. The locking elements and the drop supports include a motor/encoder assembly able to move a respective piston in direction of the sphere.

In one or more embodiments, the cooling/filtering device comprises at least one cooling box in which a controlled fan, a cooling element filled with water circulating in a closed circuit and a porous filter are inserted; every outlet pipe and every inlet pipe connects said cooling box with said isolation sealed structure.

In one or more embodiments, the group includes an electrostatic discharge device able to bring the sphere at the same electrostatic potential as the drop supports.

In one or more embodiments, the group according includes an injection device able to supply liquid to the four drop supports.

In one or more embodiments, the sphere is composed of two hemispheres screwed together for lodging inside a load.

In one or more embodiments, each locking element comprises a motor/encoder assembly and a piston operated by the motor/encoder assembly and comprising a bowl shape free end having a concavity larger than the surface of the sphere and a plurality of slots in order to let a cooling gas to cool sphere zones covered by the bowl shape free end itself.

In one or more embodiments, one of the two locking elements comprises a helicoidal spring wounded around a stem of the respective piston.

In one or more embodiments, each drop supports comprises a motor/encoder assembly and a piston operated by the motor/encoder assembly; said piston comprising at one of its ends a copper internal structure where the drops are formed and hosting a heater and a temperature sensor.

In one or more embodiments, the sphere is an experimentation room hosting an experimental equipment and a wireless board for communication.

In one or more embodiments, the sphere is made of aluminium based light alloy.

In one or more embodiments, the sphere has been undergone to a nickel plating surface treatment.

In one or more embodiments, the sphere is made of a graphite-loaded polymer.

BRIEF DESCRIPTION OF THE SEVERAL VIEWS OF THE DRAWINGS

For a better understanding of the invention an embodiment is given below purely by way of illustration and not of limitation with the aid of the accompanying drawings, wherein.

DETAILED DESCRIPTION

Figure 1:
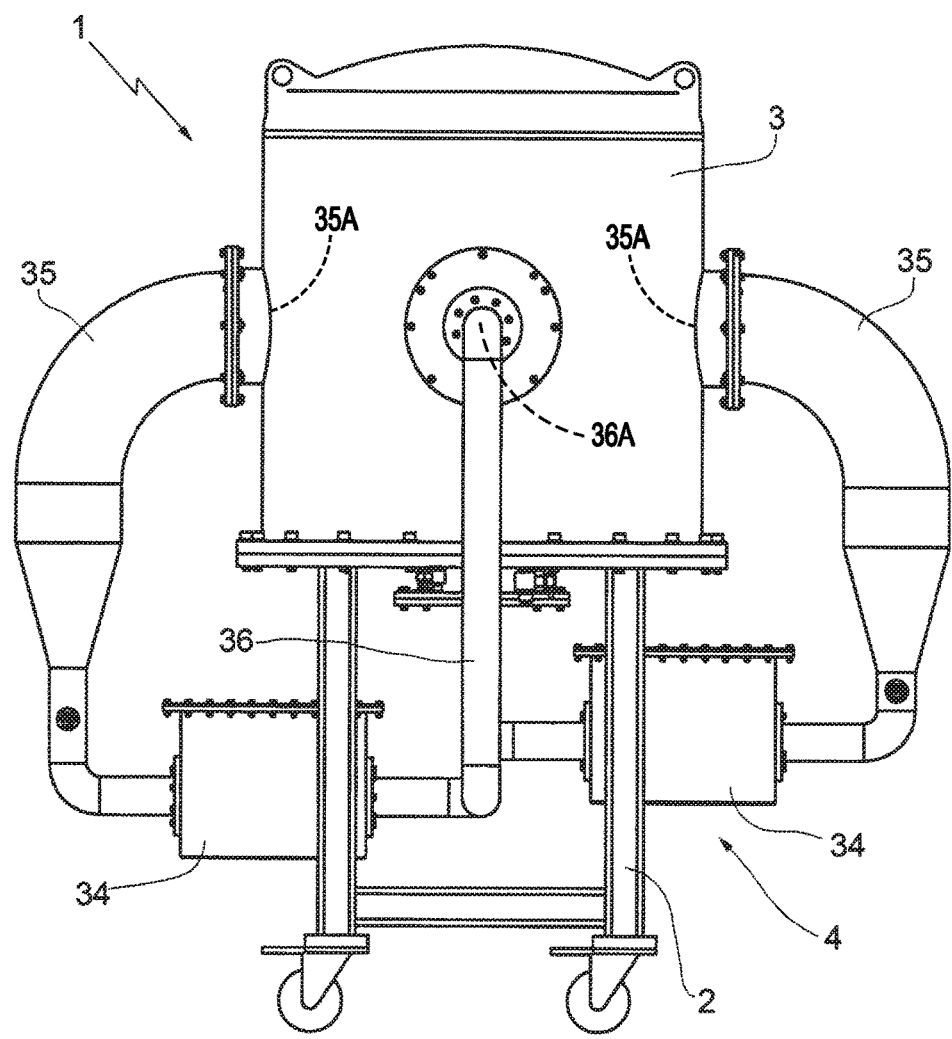
FIG. 1 is a lateral view of the group according to the present invention

The group according to the present invention is indicated in FIG. 1 as a whole with 1.

The group 1 basically comprises a support structure 2, a cylindrical isolation sealed structure 3 wherein experiments in a microgravity environment are carried out, and a cooling/filtering device 4 useful to allow the circulation of inert cool gas, for instance nitrogen, inside the isolation structure 3 as it will be explained below.

Figure 2:
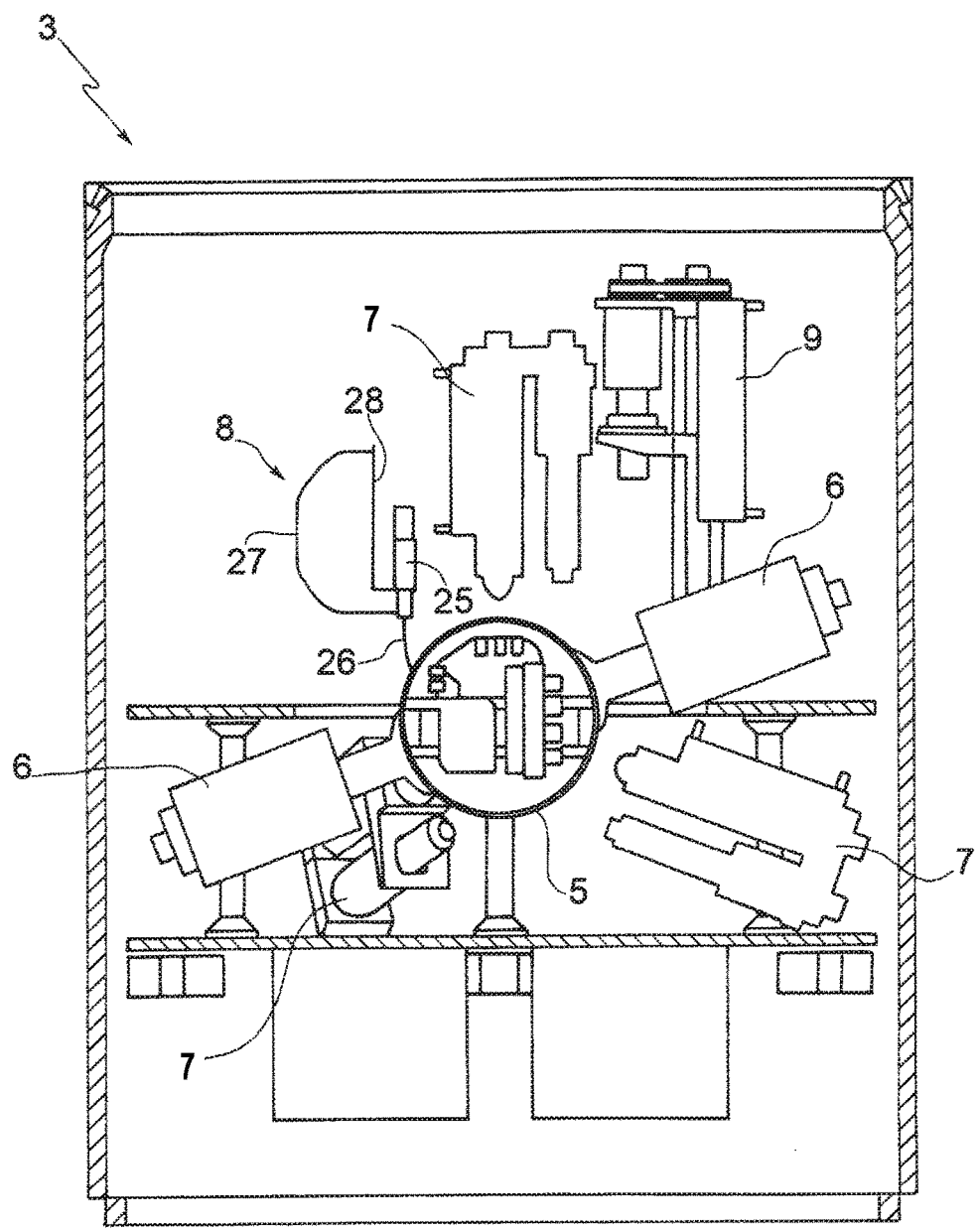
FIG. 2 is a partly cross section of a portion of the group of FIG. 1.

As it is shown in FIG. 2, inside the cylindrical isolation sealed structure 3 the group 1 comprises a sphere 5 made of aluminum based light alloy and made of two hemispheres screwed each other, two locking elements 6 acting from opposite sides on the sphere 5 and useful to keep the sphere 5 secured in a right position during a non-operational phase of the group 1, four drop supports 7 (only three of them are shown in FIG. 2) located around the sphere 5 respectively on the four vertexes of a regular tetrahedron, an electrostatic discharge device 8 able to bring the sphere 5 at the same electrostatic potential as the drop supports 7, an injection device 9 able to supply liquid to the four drop supports 7 in order to realize the respective drops. The cooling/filtering device 4 is able to cool the sphere surface at a temperature lower than that of the drops for preventing the drops to coalesce over the sphere surface, and to filter the gas around the sphere for preventing dust to deposit over the sphere surface and the drops.

In FIG. 2 drop supports 7 are not shown in section for sake of clarity because of their structural complexity.

Temperature and pressure sensors are needed to monitor the sphere surface temperature, the oil drop temperature, the gas pressure inside the sealed structure 3.

Inside the sphere 5 an experimental device is located, which communicates with the external world by means of a wireless boards set. To allow the radio signal to pass through the metallic sphere, an antenna has been properly realized and located in a groove drilled in the sphere. The antenna is located just below the geometrical surface of the sphere and is covered by a conductive epoxy resin to prevent an accumulation of electrostatic charges over the sphere surface. The roughness and smoothness of such portion of the sphere surface after resin deposition shall be the closest possible to that of the entire sphere surface.

Figure 3:
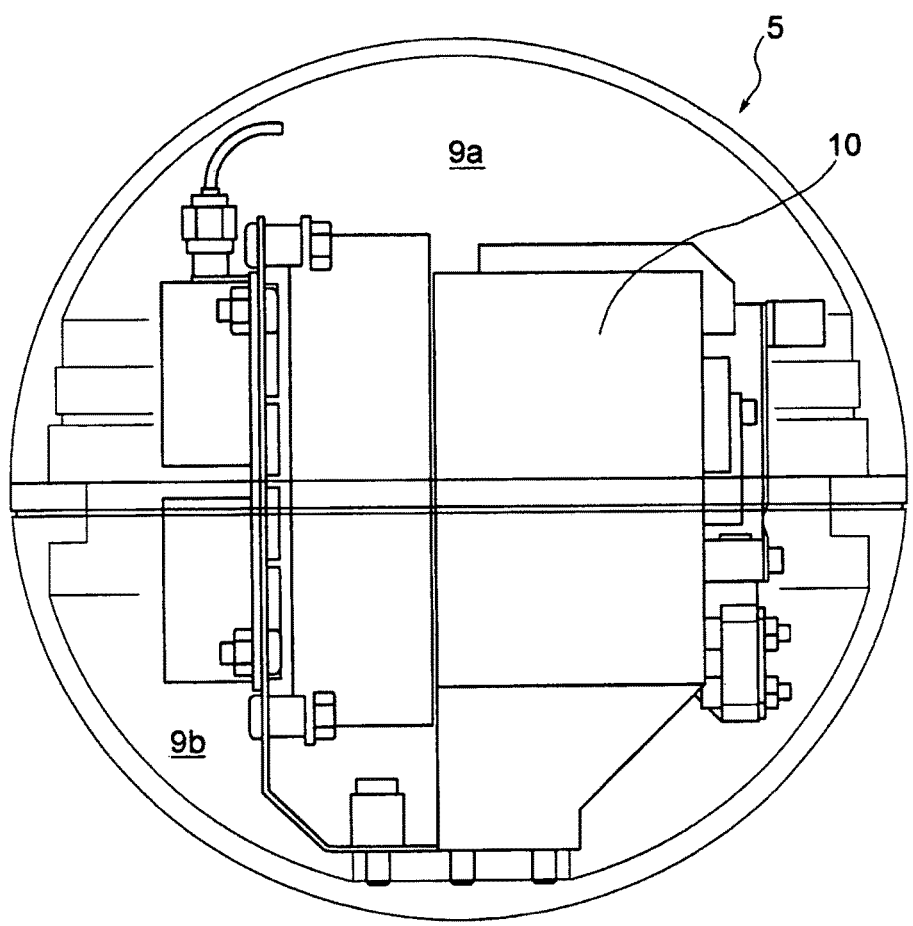
FIG. 3 is a partly transparent lateral view of a first particular of the portion of FIG. 2.

The sphere 5 has undergone a nickel plating surface treatment and, as is shown in FIG. 3, is composed of two hemisphere 9a, 9b screwed together for lodging inside the sphere itself an experimental equipment 10 and a wireless board for communication.

Differently, sphere 5 can be made of graphite or carbon-loaded polymers, which entails the advantages of a lower weight and, mainly, the transparency to radio signals; in this configuration, there is no need to have an antenna engraved on the external sphere surface.

Figure 4:
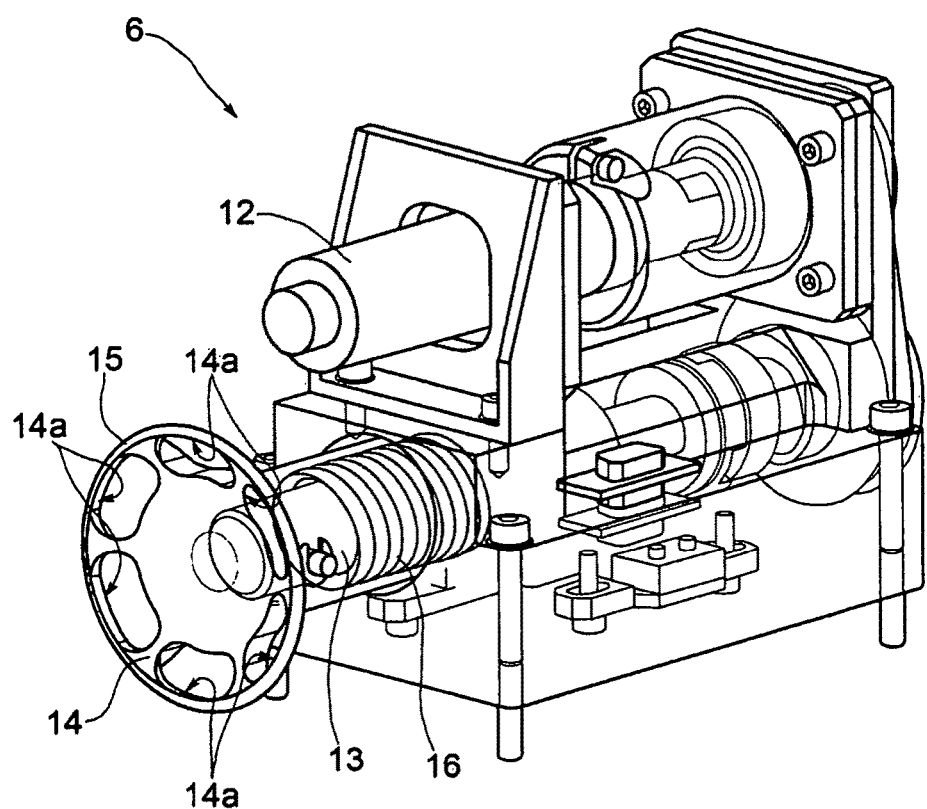
FIG. 4 is a partly transparent top perspective view of a second particular of the portion of FIG. 2.

The locking elements 6 are designed to allow sphere 5 locking during a non-operational phase without sticking or scratching the sphere surface and to be able to support the sphere load (sphere plus experimental equipment). As it is shown in FIG. 4, each locking element 6 comprises a motor/encoder assembly 12 and a piston 13 operated by the motor/encoder assembly 12 in a known way.

Each piston 13 comprises a bowl shape free end 14. In particular, in each piston 13 the bowl shape free end 14 has a concavity larger than the sphere surface and has six slots 14a. These technical features have the purpose to let the gas to cool the sphere also in zones covered by the bowl shape free end 14. In fact, each bowl shape free end 14, actually, contacts with the sphere surface only by a circumferential edge 15 allowing the cooling gas to reach basically all the sphere surface zone underneath the bowl shape free end 14.

Only one of the two locking elements 6 comprises a helical spring 16 wounded around a stem of the respective piston 13. In this way, the pressure against the sphere surface is reduced at minimum without jeopardizing the locking power of the two locking elements 6.

Figure 5:
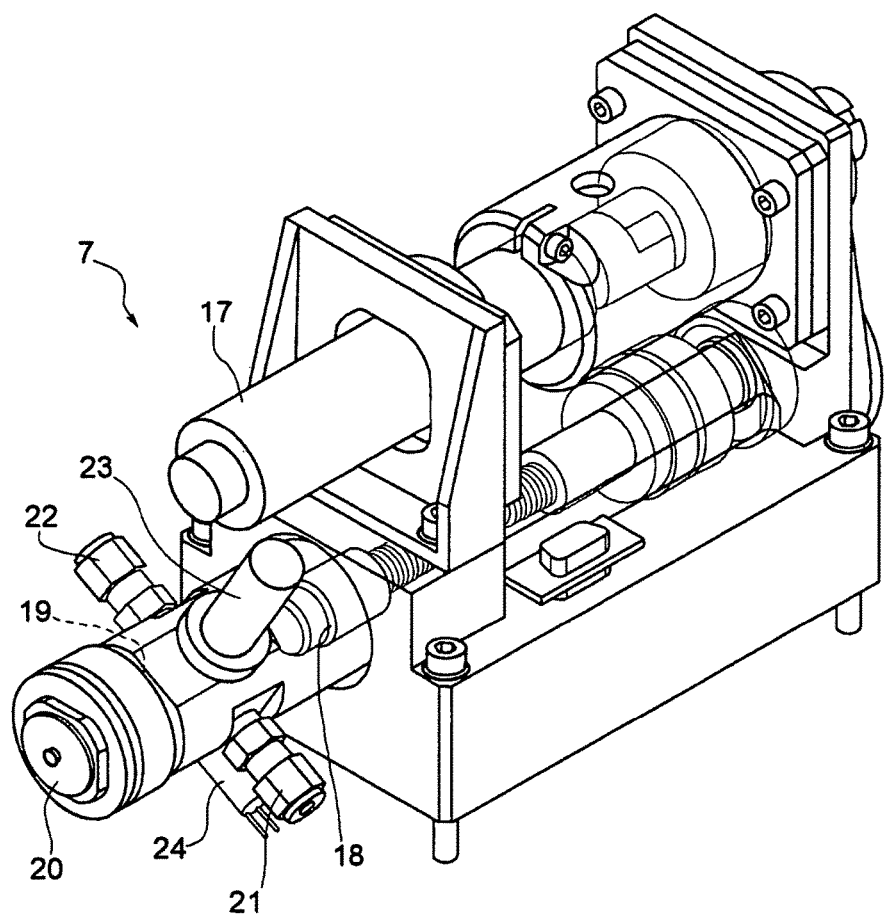
FIG. 5 is a partly transparent top perspective view of a third particular of the portion of FIG. 2.

As it is shown in FIG. 5, each drop supports 7 comprises a motor/encoder assembly 17 and a piston 18 operated by the motor/encoder assembly 17 in a known way.

Furthermore, the piston 18 comprises at one of its ends an internal structure 19 made of copper and hosting a heater and a temperature sensor. The internal structure 19 comprises an external tip 20 from which the drop is formed and which is sharp edged, machined in a truncated cone shape and with lateral surface inclined by 45°. In addition, each drop support 7 comprises a liquid inlet 21, a liquid outlet 22, a remotely controlled 2-valve 23 in order to allow the liquid circuit to be closed, and a remotely controlled 3-valve 24 in order to switch from injection to suction and vice-versa. The controlled liquid inlet 21 and liquid outlet 22 are obviously hydraulically connected with the internal structure 19.

The electrostatic discharge device 8 comprises a motor/encoder assembly 25, a thin tungsten wire 26 which is laid in a loop shape in order to improve the contact with the sphere surface, and a secondary metal wire 27 able to connect the thin metal wire 26 with a lug 28 which is fixed to a support. The purpose of the secondary metal wire 27 is to perform a ground connection through a dedicated electric harness.

In order to know when the electrostatic discharge device 8 has to be used, the group 1 comprises an electric potential meter (not shown in the Figures) for measuring the electrostatic charge on the sphere 5.

Figure 6:
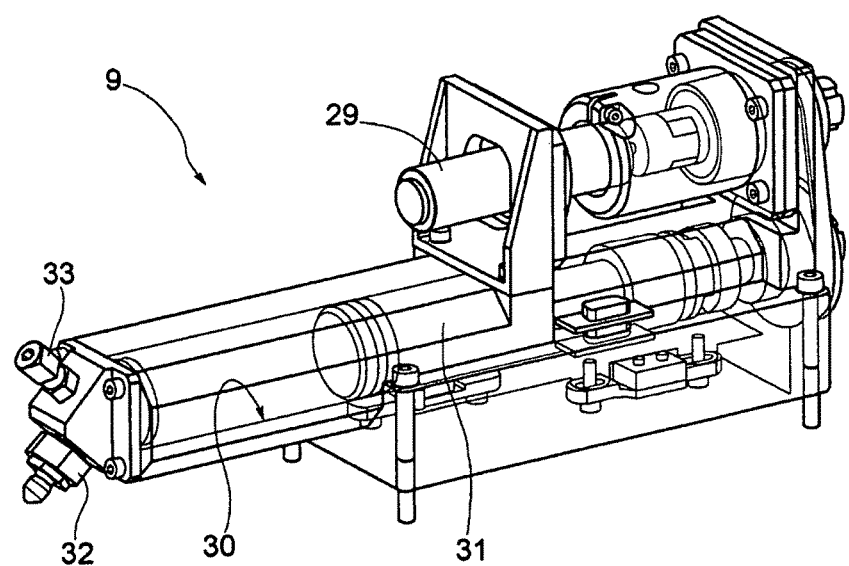
FIG. 6 is a partly transparent top prospective view of a fourth particular of the portion of FIG. 2.

As it is shown in FIG. 6, the injection device 9 comprises a motor/encoder assembly 29 and a liquid reservoir 30 wherein a piston 31 operated by the motor/encoder assembly 29 is able to move. The injection device comprises a filling valve 32 and a liquid outlet 33 facing both into the liquid reservoir 30. The liquid outlet 33 is connected with the liquid inlet 21 of the drop supports 7 by a hose. Drops shall be formed or sucked only by means of piston 31 movement and drop volume shall be controlled. Preferably, the liquids to be used for drops formation are silicon oils of different viscosity and chain length.

The stability of the non coalescing drops is strongly influenced by several factors, such as the roughness of the surface, the presence of electrostatic charge, the temperature difference between the drop and the sphere surface, the presence of dust on the sphere surface.

Regarding the constraints of keeping in place a suitable temperature difference between the drop and the sphere surface, and that of keeping the environment around the sphere and the drops free from dust, a dedicated cooling/filtering device 4 has been designed and realized. The cooling/filtering device 4 comprises two identical boxes (lungs) 34 in which a controlled fan, a cooling element filled with water circulating in a closed circuit and a porous filter are inserted. The two lungs 34 are connected to the cylindrical isolation sealed structure 3 by means of two sealed inlet pipes 35. Each of the two sealed inlet pipes 35 faces into the cylindrical isolation sealed structure 3 by a respective inlet window 35A.

Every fan lodged in a respective lung 34 creates a forced ventilation of dry, clean gas (nitrogen or other inert gases) impinging on the sphere. The gas is cooled by crossing the cooling element through which cooled liquid flows. The gas and the cooled liquid do not come into contact. The temperature of the cooling liquid may be adjusted to get the suitable efficiency of the gas cooling jet.

In order to prevent misalignment of the sphere due to the gas flow, the two inlet windows have been realized opposite one another. The gas jets may be controlled in order to have a net zero momentum impinging on the sphere. The gas current and temperature are monitored by means of dedicated flow-meters and temperature sensors.

The gas injected into the structure is sucked by two opposite outlet pipes 36 (only one is shown in FIG. 1) each of them faces into the cylindrical isolation sealed structure 3 by a respective outlet window 36A placed 90 degrees far from each of the inlet windows. Every outlet pipe 36 connects the cylindrical isolation sealed structure 3 to a respective lung 34. Specifically, every outlet pipe 36 draws gas from the cylindrical isolation sealed structure 3 and discharges it into a respective lung 34.

Basically, the cooling/filtering device 4 consists of two identical lines, each of them works for injecting a cool/filtered gas into the cylindrical isolation sealed structure 3 and sucking gas from the cylindrical isolation sealed structure 3.

Every inlet windows has a diameter of about 20 mm larger than the diameter of the sphere, in order to avoid the jets could impinge only on part of the sphere. In this way, all the sphere surface section is always covered by a uniform gas flow. Suitable diverging elements have been inserted into the pipes to allow the gas jet to impinge over the entire sphere surface. The novel cooling/filtering device is part of the invention and is essential for the correct functioning of the main device for long duration experiments. It provides both the functions of filtering and cooling the gas before it enters the chamber where the sphere is suspended. The cooling effect is obtained by the gas impinging on the sphere surface. The sphere indeed has not to be touched by any mechanical constraints, otherwise its isolation characteristic would be lost.

In use, the sphere 5 is blocked in its right position inside the isolation sealed structure 3 by the two locking elements 6 as it is shown in FIG. 2.

The air present inside the structure is evacuated by means of a vacuum pump, connected to the main structure 3 through a dedicated valve. Once a residual pressure of no more than 1 mbar is reached inside the sealed structure 3, the vacuum pump is disconnected and the structure 3 connected to a filling line with inert gas by means of another dedicated valve. The structure is then filled with inert gas until an overpressure of 200 mbar is reached with respect to the ambient one. At this point the filling line is also closed and the pressure inside the structure 3 monitored by means of a dedicated digital manometer. The filtering/cooling system is then activated to cool and filter the gas. The gas is injected into the structure 3 through lines 35 and sucked through lines 36 for being filtered and cooled again. The minimum working overpressure is set to 50 mbar with respect to the ambient one.

Starting from this situation, the injection device 9 injects silicon oil into each of the four drop supports 7 which proceed to form respective drops. Preferably, the used silicon oil is characterized by a viscosity value of 5 cSt. The drops shall of course be heated with the dedicated heater hosted into the copper internal structure 21. The temperature of the heater should be settable and controllable. In particular, once the drop is formed, the heater starts heating it up to 55° C.-60° C. A sensor, not shown in the Figures, monitoring the temperature of the drop, will help understanding when the set temperature is reached. At the same time, the sphere 3 is brought at a temperature lower than that of the drop by means of the cooling/filtering device 4.

After having verified that the thermal condition are satisfied, the operator moves the drop supports to approach slowly the drop to the sphere surface until the contact is established. In particular, each motor/encoder 17 brings the respective formed drop into contact with the sphere surface. Actually, the drops only apparently touch the sphere surface. Once the contact is established with all the drops, these are slightly squeezed against the sphere.

At this point, the operator moves back the locking elements to release the sphere, which is now free to move with respect to the drops being supported by them without friction.

This invention may reveal particularly useful as a new device that could be embarked onboard microgravity platforms to perform experiments sensitive to rotating force fields that could compromise the experimental results. Indeed, while orbiting around Earth, platforms offer an environment with reduced gravity levels (i.e. the microgravity environment); however such desired condition is accompanied by several undesired effects that may sometime affect seriously the results of the experiment under study.

Differently of what is described above, the number of drops can be also higher than four, placed in a symmetrical way around the sphere. The higher the number of drops, the higher the mass of the sphere that can be sustained.

Normally on ground it is easily to form drops by 3-4 mm in diameter. An upper limit may be set to 5 mm in diameter, larger sizes becoming unstable due to the gravity field. In an environment with reduced gravity levels it is possible to generate stable larger drops (by 20 mm in diameter or larger) necessary to sustain the load, whose amount will depend upon the number of drops foreseen for the facility.

The group of the present invention can also solve the problems related to the presence of vibrations that are transmitted to the experimental devices, and the presence of the residual gravity vector, that cannot be eliminated because of the intrinsic characteristics of the space flights.

The peculiarity of the group of the present invention is not only the capability of orienting the sphere and the h/w located inside it with respect to any rotating field imposed to the sphere itself, but also the possibility to adapt the sphere without friction, i.e. without any inertial effect due to the presence of mechanical joints (like those, for instance, of a gyroscope). For instance, for allowing the sphere to orient with respect to the residual gravity vector present onboard orbiting spaceships, it is necessary and enough to locate the experimental payload inside the sphere in such a way to have the center of mass not coincident with the geometrical center of the sphere.

This device also offers the capability of providing a space environment with improved characteristics of vibration damper; the drops themselves indeed are quasi-perfect vibration isolators against high frequencies disturbance.

In conclusion, the group of the present invention offers an innovative solution for allowing the free orientation, i.e. without friction and physical or mechanical constraints, of spherical bodies with respect to a force field (the residual gravity for instance) acting on the sphere itself.

The present invention refers to a physical group (equipment) for realizing experiments of free orientation of a sphere with respect to outside force fields, and the working parameters to be used in this group can be set by technicians on the basis of specific experimental situations. The group also offers characteristics of vibration isolator.

In other words, because of the subject of the invention is a physical group, the described example of the invention consists in a description of a preferred embodiment of the equipment in reference to FIGS. 1-6. No examples of working parameters are described because the subject of the invention is not a method but the physical equipment.

In addition, the group of the present invention is designed to be used in space environment and it would be nonsense to describe working parameters adapted to a ground environment.

The invention claimed is:

1. A group for allowing free orientation of a sphere with respect to outside force fields comprising:
    a support structure,
    a sphere,
    two locking elements acting from opposite sides on the sphere and useful to keep the sphere in a right position during a non-operational phase of the group,
    at least four drop supports located symmetrically around the sphere and able to form drops and to keep them at a desired temperature,
    an isolation sealed structure useful to isolate said sphere, said two locking elements, and said at least four drop supports from the surrounding and to prevent dust deposition on the sphere surface and on drops realized by said drop supports, and
    a cooling and filtering device useful to inject cool gas inside the isolation structure in order to keep the sphere at a temperature lower than that of the drops; said cooling/filtering device comprising at least two inlet pipes respectively facing into said isolation sealed structure through respective inlet windows placed opposite one another with respect to the sphere in order to invest from opposite sides the sphere by a cooled and filtered gas, and at least two outlet pipes respectively facing into the isolation sealed structure through respective outlet windows placed 90 degrees far from each of the inlet windows; said locking elements and said drop supports each comprising a respective motor/encoder assembly able to move a respective piston toward the sphere.

2. The group according to claim 1, wherein said cooling and filtering device comprises first and second cooling boxes in which a controlled fan, a cooling element filled with water circulating in a closed circuit and a porous filter are inserted; a first outlet pipe of the at least two outlet pipes and a first inlet pipe of the at least two inlet pipes connects said first cooling box with said isolation sealed structure and a second outlet pipe of the at least two outlet pipes and a second inlet pipe of the at least two inlet pipes connects said second cooling box with said isolation sealed structure.

3. The group according to claim 1, comprising an electrostatic discharge device able to bring the sphere at the same electrostatic potential as the drop supports.

4. The group according to claim 1, comprising an injection device able to supply liquid to the four drop supports.

5. The group according to claim 1, wherein said sphere is composed of two hemisphere screwed together for lodging a load inside.

6. The group according to claim 1, wherein each locking element comprises a motor/encoder assembly and a piston operated by the motor/encoder assembly and comprising a bowl shape free end having a concavity larger than the surface of the sphere and a plurality of slots in order to let a cooling gas to cool sphere zones covered by the bowl shape free end itself.

7. The group according to claim 6, wherein one of the two locking elements comprises a helical spring wound around a stem of the respective piston.

8. The group according to claim 1, wherein each drop support comprises a motor/encoder assembly and a piston operated by the motor/encoder assembly; said piston comprising at one end a copper internal structure where the drops are formed and hosting a heater and a temperature sensor.

9. The group according to claim 1, wherein said sphere is an experimentation room hosting an experimental equipment and a wireless board for communication.

10. The group according to claim 1, wherein said sphere is made of aluminium based light alloy.

11. The group according to claim 10, wherein said sphere has been undergone to a nickel plating surface treatment.

12. The group according to claim 1, wherein said sphere is made of a graphite-loaded polymer.

* * * * *